United States Patent [19]
Batt et al.

[11] Patent Number: 4,859,693
[45] Date of Patent: Aug. 22, 1989

[54] ANTIINFLAMMATORY CARBINOLOIMIDAZOLES

[75] Inventors: Douglas G. Batt, Wilmington, Del.; Richard S. Greenberg, Wayne, N.J.; Richard R. Harris, Wilmington, Del.

[73] Assignee: E. I. Du Pont de Nemours and Company, Wilmington, Del.

[21] Appl. No.: 230,448

[22] Filed: Aug. 10, 1988

[51] Int. Cl.$^4$ .............................................. A61K 00/00
[52] U.S. Cl. ................................................... 514/397
[58] Field of Search ......................................... 514/397

[56] References Cited

U.S. PATENT DOCUMENTS

| | | | |
|---|---|---|---|
| 4,239,765 | 12/1980 | Regel et al. | 424/269 |
| 4,285,961 | 8/1981 | Prucher et al. | 424/273 |
| 4,301,166 | 11/1981 | Regel et al. | 424/269 |
| 4,358,458 | 11/1982 | Scharwachter et al. | 424/273 |
| 4,413,003 | 11/1983 | Miller et al. | 424/273 |
| 4,414,210 | 11/1983 | Miller et al. | 424/245 |
| 4,472,415 | 9/1984 | Worthington et al. | 424/269 |
| 4,480,114 | 10/1984 | Regel | 549/563 |
| 4,569,935 | 2/1986 | Rosenberg et al. | 514/282 |
| 4,689,337 | 8/1987 | Bushell | 514/359 |

FOREIGN PATENT DOCUMENTS

| | | |
|---|---|---|
| 168982 | 10/1981 | Australia . |
| 0158448 | 10/1985 | European Pat. Off. . |
| 0165783 | 12/1985 | European Pat. Off. . |
| 2920375 | 11/1980 | Fed. Rep. of Germany . |
| 2110684 | 6/1983 | United Kingdom . |
| 2156807 | 10/1985 | United Kingdom . |

OTHER PUBLICATIONS

*Biochemical Pharmacology*, vol. 35, No. 6, pp. 883–891, 1986 (Great Britain).

*Primary Examiner*—Stanley J. Friedman

[57] ABSTRACT

Antiinflammatory carbinoloimidazoles are provided which have the formula:

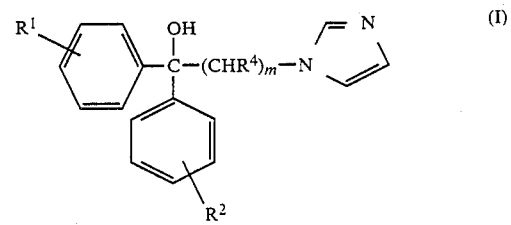

or a pharmaceutically acceptable salt thereof, wherein
$R^1$ and $R^2$ independently are H, F, Cl, Br, $CH_3$, $CF_3$ or $S(O)_n R^3$ where n is 0, 1 or 2 and
$R^3$ is alkyl of 1–4 carbon atoms;
$R^4$ is H or alkyl of 1–4 carbon atoms with the proviso that $R^4$ is H when m is 2 or 3; and
m is 1 to 3.

The carbinoloimidazoles are preferably administered as topical antiinflammatory compositions.

10 Claims, No Drawings

ANTIINFLAMMATORY CARBINOLOIMIDAZOLES

FIELD OF THE INVENTION

This invention relates to pharmaceutical compositions which contain carbinoloimidazoles, and more particularly to such compositions which are topical antiinflammatory compositions.

BACKGROUND OF THE INVENTION

The antifungal and insecticidal properties of carbinoloazoles are well documented in the patent literature.

U.S. Patent No. 4,689,337, issued to Bushnell et al. on Aug. 25, 1987, GB 2,156,807A, and European Patent No. 0 158 448, issued to Bushnell et al. on Oct. 16, 1985, discloses, among others, compounds of the formula:

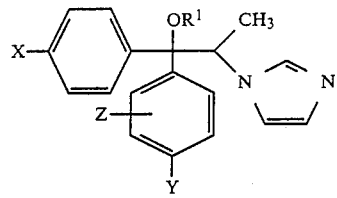

wherein $R^1$ is hydrogen, alkyl of up to six carbon atoms or carboxylic acyl of up to ten carbon atoms; and X, Y and Z are each selected from halo, $CHF_2$, $CF_3$, $OCHF_2$ and $OCF_3$, and Z may also be H. The compounds are disclosed as having both fungicidal and insecticidal activity.

German Patent No. DE 29 20 375, issued to Regel et al. on Nov. 20, 1980, discloses fungicides of the formula:

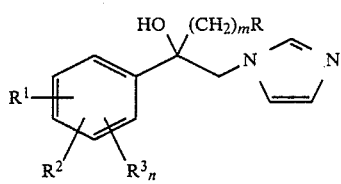

wherein

R is optionally substituted phenyl, naphthyl or tetrahydronaphthyl;

$R^1$ is optionally substituted phenyl or cycloalkyl;

$R^2$ is hydrogen, or $R_1$ and $R_2$ together, in the ortho position relative to each other, denote an optionally substituted multimembered methylene bridge, or together with the phenyl ring denote naphthyl;

$R^3$ is halogen, alkyl, alkoxy, or haloalkyl; n is 0, 1, 2 or 3; and m is 0 or 1.

U.S. Pat. No. 4,239,765, issued to Regel et al. on Dec. 16, 1980, describes antimycotic compounds including those of the formula:

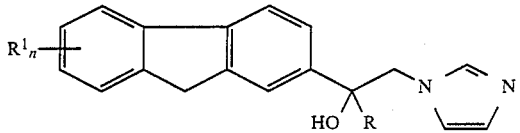

wherein

R is an optionally substituted phenyl, benzyl, naphthyl, naphthylmethyl, tetrahydronaphthyl, or tetrahydronaphthylmethyl;

$R^1$ is halogen or alkyl; and n is 0, 1, or 2.

U.S. Pat. No. 4,301,166, issued to Regel et al. on Nov. 17, 1981, discloses antimycotic compounds of the formula:

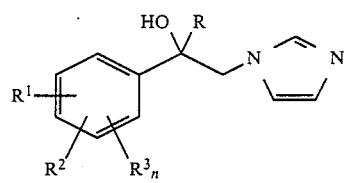

wherein

R is optionally substituted phenyl, naphthyl, or tetrahydronaphthyl;

$R^1$ is optionally substituted phenyl or cycloalkyl;

$R^2$ is hydrogen, or $R_1$ and $R_2$ together, in the ortho position relative to each other, denote an optionally substituted multimembered methylene bridge, or together with the phenyl ring denote naphthyl;

$R^3$ is halogen, alkyl, alkoxy, or haloalkyl; and n is 0, 1, 2 or 3.

U.S. Pat. No. 4,480,114, issued to Regel on Oct. 30, 1984, discloses a process for the preparation of compounds of U.S. Pat. 4,301,166.

U.S. Pat. No. 4,358,458, issued to Scharwachter et al. on Nov. 9, 1982, claims compounds of the formula;

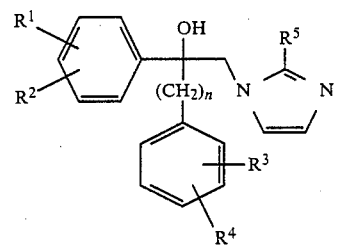

wherein $R^1$, $R^2$, $R^3$ and $R^4$ may be independently hydrogen, halogen, $C_1$ to $C_4$ alkyl or $C_1$ to $C_4$ alkoxy;

$R^5$ is hydrogen or $C_1$ to $C_3$ alkyl;

n is 0 or 1;

and pharmaceutically acceptable salts thereof. These compounds are claimed as useful for treatment of infections caused by fungi and yeasts.

U.S. Pat. No. 4,413,003, issued to Miller et al. on Nov. 1, 1983, discloses agricultural fungicides of the formula:

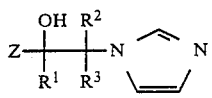

wherein
Z is an aryl or substituted aryl; and $R^1$, $R^2$ and $R^3$ are independently hydrogen, cyano, alkyl, cycloakly, alkenyl, cycloalkenyl,
alkynyl, aryl, or substituted aryl. U.S. Pat. No. 4,414,210, issued to Miller et al. on Nov. 8, 1983, discloses agricultural fungicides of the formula:

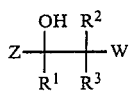

wherein
W is a 1- or 4-(1,2,4-triazole); and Z, $R^1$, $R^2$ and $R^3$ are the same as above for U.S. Pat. No. 4,413,003.
U.S. Pat. No. 4,472,415, issued to Worthington et al. Sept. 18, 1984, discloses triazoles of the formula:

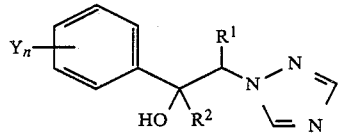

wherein
$R^1$ is hydrogen, $C_1$ to $C_8$ akly, benzyl, or benzyl substituted with halogen, $C_1$ to $C_4$ alkyl, nitro, trifluoromethyl, cyano, methoxy, ethoxy, phenyl, or methylenedioxy;
$R^2$ is hydrogen or $C_1$ to $C_8$ alkyl;
Y is independently hydrogen, halogen, nitro, $C_1$ to $C_4$ alkyl, $C_1$ to $C_4$ alkoxy, unsubstituted amino or methyl- or ethylamino; and
n is 1 or 2.
These compounds are claimed as agricultural fungicides.
U.K. Patent No. GB 2 110 684 A, issued to Nyfeler et al. on June 22, 1983, discloses compounds of the formula:

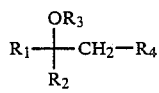

wherein
$R_1$ is phenyl, phenyl mono- to trisubstituted by halogen, $C_1$ to $C_3$ haloalkyl, nitro, $C_1$ to $C_3$ alkoxy, $C_1$ to $C_8$ alkyl and/or cyano, or phenyl substituted by phenyl or phenoxy, naphthyl or naphthyl mono- or disubtituted by halogen, nitro and/or $C_1$ to $C_3$ aklyl, benzyl, or benzyl mono- or disubstituted by halogen, nitro, and/or $C_1$ to $C_3$ alkyl;
$R_2$ is phenyl, phenyl mono- to trisubstituted by halogen, $C_1$ to $C_3$ haloalkyl, nitro, $C_1$ to $C_3$ alkoxy, $C_1$ to $C_8$ alkyl and/or cyano, or phenyl substituted by phenyl or phenoxy, or it is $C_1$ to $C_{10}$ alkyl, $C_3$ to $C_8$ cycloalkyl or $C_3$ to $C_8$-cycloalkyl-($C_1$ to $C_4$ alkyl);

$R^3$ is $C_1$ to $C_{12}$ alkyl, $C_2$ to $C_4$ alkenyl, $C_3$ to $C_4$ alkynyl, benzyl, or benzyl mono- or disubstituted by halogen, nitro and/or $C_1$ to $C_3$ alkyl; and
$R_4$ is an azole group, including acid addition salts thereof, quaternary azolium salts, and metal complexes.
These compounds are diclosed as novel agricultural fungicides.
European Patent No. 0 165 783, issued to Hirsch et al. on Dec. 27, 1985, discloses compounds of the formula:

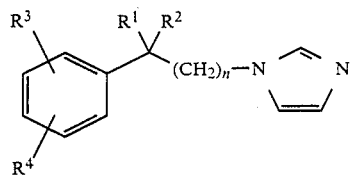

wherein
n is 1 or 2;
$R^1$ is H, OH or $OCH_2R^5$;
$R^2$ is H or

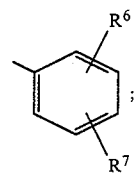

$R^5$ is vinyl, thienyl, halothienyl or

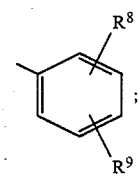

and
$R^3$, $R^4$, $R^6$, $R^7$, $R^8$ and $R^9$ are independently H, $OCH_3$, halogen, $CF_3$, or $NO_2$, or a
pharmaceutically acceptable salt thereof.
These compounds are disclosed as aromatase inhibitors for treatment and prevention of estrogen-dependent diseases.
Australian Patent No. AU-A1-68 982/81, issued to Boshagen et al. on Oct. 8, 1981, discloses, among others, compounds of the formula:

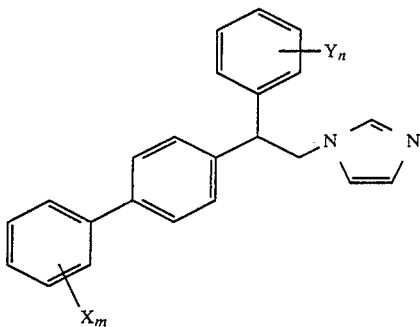

wherein
 X is halogen, alkyl, haloalkyl, alkoxy, alkylthio, nitro, or cyano;
 Y is halogen, alkyl, haloalkyl, alkoxy, alkylthio, nitro, cyano or optionally substituted phenyl; and
 m and n are independently 0, 1, 2 or 3.

The compounds are disclosed as antimycotic agents, and their synthesis is claimed from carbinols of the formula:

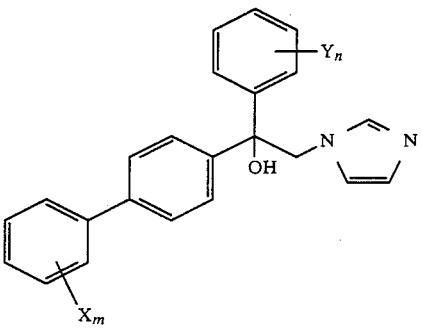

wherein
 X, Y, m and n are the same as above.

U.S. Pat. No. 4,285,961, issued to Prucher et al. on Aug. 25, 1981, is a patent describing various pharmacological preperties, including an antiphlogistic effect, of basic thioethers. Among the compounds disclosed are compounds of the formula:

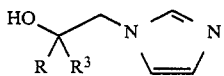

wherein
 $R^3$ is phenyl;
 R is dibenzothienyl or p-$R^5$-S-phenyl;
 $R^5$ is phenyl, benzyl or akly; and
 n is 1, 2 or 3.

U.S. Pat. No. 4,569,935, issued to Rosenberg et al. on Feb. 11, 1986, describes the use of ketoconazole in the treatment of psoriasis in humans.

None of the above-mentioned references suggests the antiinflammatory utility of the compounds of this invention.

SUMMARY OF THE INVENTION

According to the present invention there is provided a pharmaceutical composition consisting essentially of a suitable pharmaceutical carrier and an antiinflammatory amount of a compound of the formula:

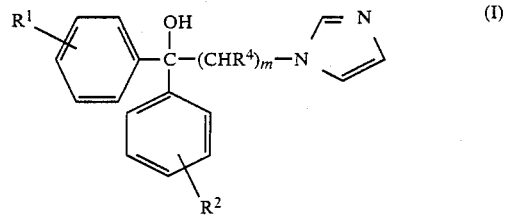

or a pharmaceutically acceptable salt thereof,
wherein
 $R^1$ and $R^2$ independently are H, F, Cl, Br, $CH_3$, $CF_3$ or $S(O)_nR^3$ where n is 0, 1 or 2 and $R^3$ is alkyl or 1–4 carbon atoms;
 $R^4$ is H or alkyl of 1–4 carbon atoms with the proviso that $R^4$ is H when m is 2 or 3; and
 m is 1 to 3.

Also provided is a method of treating inflammation in a mammal comprising administering to the mammal an antiinflammatory amount of a compound of Formula (I).

Further provided is the above composition as and the above method administered as a topical composition.

When $R^4$ is alkyl in compounds of Formula (I), two enantiomers are possible. Thus, compounds useful in the present invention include the pure enantiomers, i.e., the (R) and (S) enantiomers, and mixtures thereof including racemates.

PREFERRED EMBODIMENTS

Preferred compounds of Formula () are those where:
(1) m is 1 and $R^4$ is $CH_3$; and/or
(2) $R^1$ and $R^2$ are both 4-Cl or 4-F.
Specifically preferred compounds are:
(1) 1,1-bis(4-chlorophenyl)-2-(1-imidazolyl)propanol
(2) 1,1-bis(4-fluorophenyl)-2-(1-imidazolyl)propanol.

DETAILED DESCRIPTION OF THE INVENTION

Synthesis

The compounds of Formula (I) wherein m is 2 or 3 can be prepared by reacting ethyl esters of Formula (II) with an appropriate aryl organometallic reagent as shown in Scheme 1.

Scheme 1

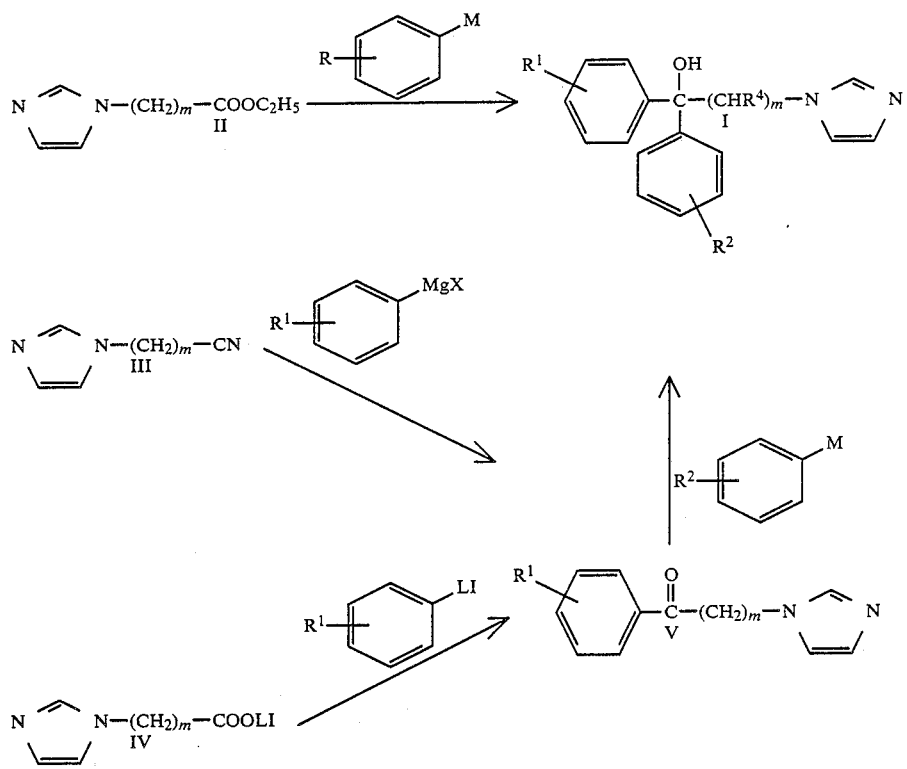

The ethyl moiety of the esters of Formula (II) can be replaced by another alkyl group such as methyl. Examples of suitable organometallic reagents are arylmagnesium halides and aryllithiums. In the case where $R^1$ and $R^2$ are different groups, reaction of a nitrile of Formula (III) with an appropriate arylmagnesium halide, or of a lithium carboxylate of Formula (IV) with an appropriate aryllithium may be used to provide, after hydrolysis, an intermediate aryl ketones of Formula (V). Reaction of these intermediates with an appropriate organometallic reagent such as an arylmagnesium halide or an aryllithium then provides a compound of Formula (I). Such reactions of organolithiums and organomagnesium halides with esters, nitriles and lithium carboxylates, which are well known in the chemical literature, are generally performed in a suitable solvent such as tetrahydrofuran or diethyl ether at a temperature ranging from about $-80°C$. to the boiling point of the solvent.

The intermediates of Formula (II) can be prepared by reaction of imidazole with a base such as sodium hydride in a suitable solvent such as benzene, followed by reaction of this salt with a suitable alkyl ester of 3-bromopropionic acid or 4-bromobutyric acid. An example of this procedure, used to prepare the compound of Formula (II) wherein m is 2, may be found in *J Polymer Sci, Polym Chem Ed* 23, 265 (1985). The same general procedure may be used to prepare intermediates of Formulas (III) and (IV).

The compounds of Formula (I) wherein m is 1 and $R^4$ is H can be prepared by reacting a chlorohydrin of Formula (VI) or an epoxide of Formula (VII) or a mixture of these two compounds with imidazole in the presence of a suitable base such as potassium tert-butoxide, sodium methoxide, potassium carbonate, or sodium hydride. These reactions are summarized in Scheme 2.

Scheme 2

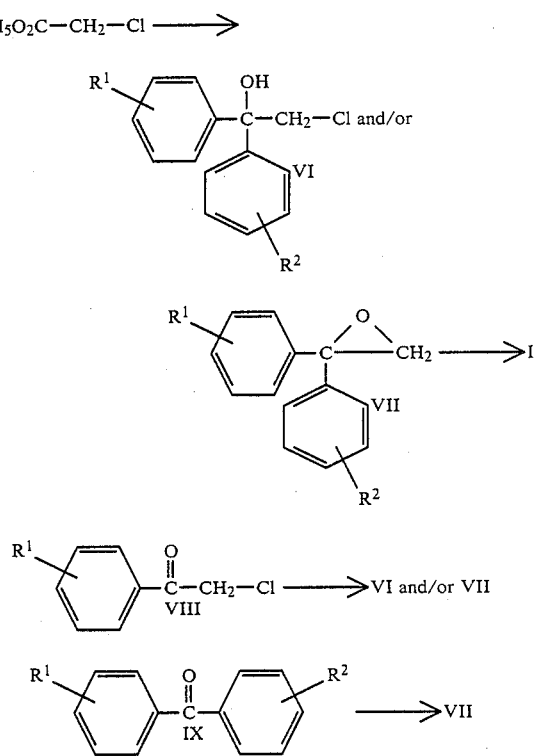

Such reactions are generally conducted in a suitable solvent, such as N,N-dimethylformamide, at a temperature between room temperature and the boiling point of the solvent. An excess of imidazole and of the base is generally used. A cation sequestering agent such as 18-crown-6 may also be used to facilitate the reaction. A preformed salt of imidazole, such as the potassium, sodium or lithium salt, may be used in place of the combination of imidazole and the suitable base.

In the case where $R^1$ and $R^2$ are the same, the intermediates of Formulas (VI) and (VII) may be prepared from ethyl chloroacetate or from another alkyl chloroacetate ester, by treatment with at least two molar equivalents of a suitable organometallic reagent. In the case where $R^1$ and $R^2$ are different, the intermediates of Formulas (VI) and (VII) may be prepared from an alphachloroacetophenone (VIII) by treatment with at least one equivalent of a suitable organometallic reagent. Such reactions may, depending upon the conditions used, yield either the chlorohydrin of Formula (VI), or the epoxide of Formula (VII), or a mixture of these two intermediates. Either of these intermediates may be used as the starting material for the preparation of a compound of Formula (I) using the procedure described above. The epoxides of Formula (VII) may also be prepared by treatment of the appropriate benzophenone of Formula (IX) with a methylene-donating reagent such as dimethylsulfoxonium methylide. The latter reaction may be used to prepare, ultimately, compounds of Formula (I) where $R^1$ and $R^2$ are either the same or different.

The compounds of Formula (I) wherein m is 1 and $R^4$ is alkyl may be prepared by reacting a compound of Formula (X) with imidazole in the presence of a suitable base, or with an alkali metal salt of imidazole, as shown in Scheme 3.

prepared by reaction of a benzophenone of Formula (IX) with a triphenylphosphine alkylide (the Wittig reaction). This reaction is well known in the chemical literature.

Compounds of Formula (I) wherein $R^4$ is alkyl may exist as racemic mixtures, or as pure enantiomers, or as non-racemic mixtures of these enantiomers. The separate enantiomers of Formula (I) may be prepared from racemic mixtures, prepared using the method described above, through standard resolution techniques which are well known in the literature. Alternatively, the separate enantiomers may be prepared in optically pure form by different synthetic routes, starting with optically pure starting materials.

Optically active compounds of Formula (I) wherein $R^1$ and $R^2$ are the same, m is 1, and $R^4$ is alkyl may be prepared, using the same reaction described above, from optically active epoxides of Formula (X) having the opposite absolute configuration at the chiral carbon. The optically active epoxides of Formula (X) may be prepared from optically active ethyl 2-chloroalkanoates of Formula (XII), which have the opposite absolute configuration at the chiral center, by reaction with suitable organometallic reagents. The ethyl moiety of these esters may be replaced by a different alkyl group. Such optically active alpha-chloroalkanoic acid esters are described in the chemical literature. Under certain reaction conditions, the intermediate chlorohydrins of Formula (XIII) may be isolated instead of the epoxides of Formula (X). These intermediates may be used in place of the epoxides of Formula (X) in the reaction leading to the optically active compounds of Formula (I), since under the conditions of this reaction, compounds of Formula (XIII) are converted to compounds of Formula (X) with the proper absolute configuration.

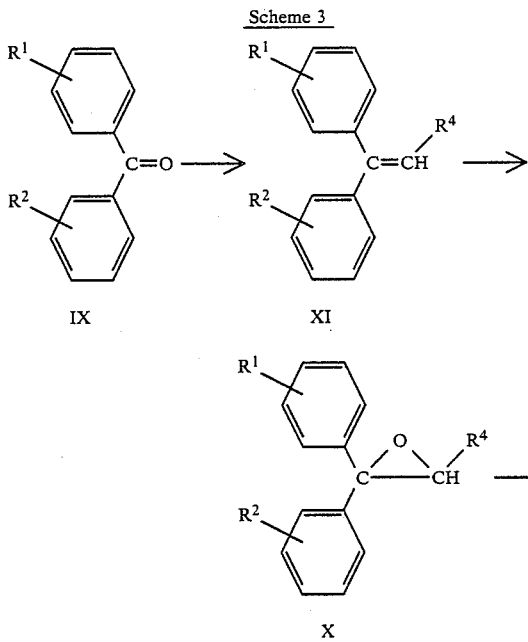

Scheme 3

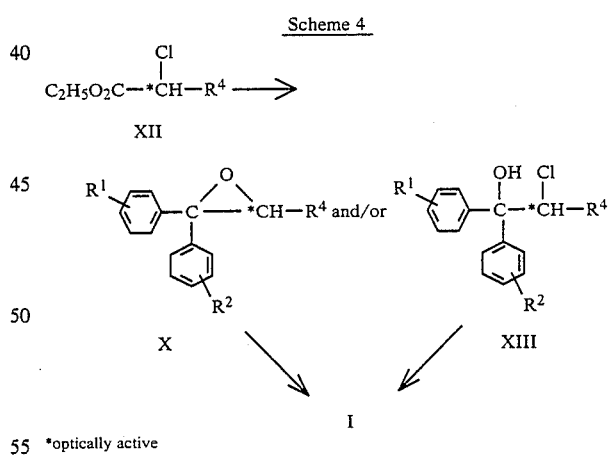

Scheme 4

*optically active

The intermediate epoxides of Formula (X) may be prepared by oxidation of the corresponding compounds of Formula (XI), using methods described in the chemical literature. Reagents for affecting this oxidation include peroxy acids such as peracetic acid and m-chloroperbenzoic acid. An intermediate of Formula (XI) may be The preferred method for preparing compounds of Formula (I) wherein $R^1$ and $R^2$ are the same, m is 1, $R^4$ is methyl, and the chiral center has the (R) absolute configuration, uses the reaction sequence shown in Scheme 4 starting with (R)-ethyl 2-chloropropionate. This compound may be prepared from (S)-ethyl lactate as described in the chemical literature.

Optically active compounds of Formula (I) wherein $R^1$ and $R^2$ are the same, m is 1, and $R^4$ is alkyl may also be prepared from optically active vicinal dihydroxy compounds of Formula (XIV) by a two-step procedure as shown in Scheme 5. The first step involves the conversion of a dihydroxy compound of Formula (XIV) to a monomethanesulfonate ester of Formula (XV), using standard procedures well known in the chemical literature. Other sulfonic acid esters, prepared analogously, may be used instead of the methanesulfonate ester. The second step consists of treatment of an intermediate of Formula (XV) with imidazole in the presence of a suitable base, or with an alkali metal salt of imidazole, using the same reaction conditions described previously. Such treatment of a compound of Formula (XV) causes conversion to an optically active epoxide of Formula (X), having the opposite absolute configuration, which is not isolated. This epoxide then reacts with imidazole or alkali metal salt of imidazole to provide a compound of Formula (I).

The optically active dihydroxy compounds of Formula (XIV) may be prepared from optically active ethyl 2-hydroxyalkanoates of Formula (XVI) by treatment with an excess of an aryl organometallic reagent, as described previously. The ethyl group of the compound of Formula (XVI) may be replaced by a different alkyl group. Optically active alphahydroxyalkanoic acid esters are well known in the chemical literature.

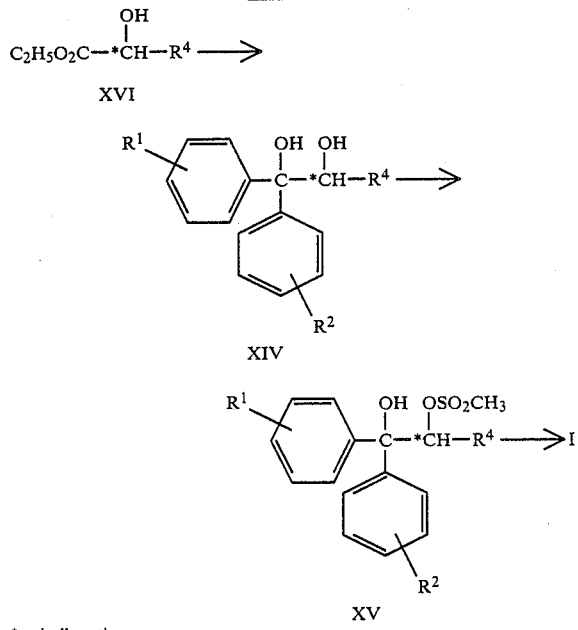

*optically active

A preferred method for preparing compounds of Formula (I) wherein $R^1$ and $R^2$ are the same, m is 1, $R^4$ is methyl, and the chiral center has the (S) absolute configuration, uses the reaction sequence shown in Scheme 5 starting with (S)-ethyl lactate.

Compounds of Formula (I) wherein $R^1$ or $R^2$ is a sulfoxide or sulfone group may be prepared from the corresponding sulfides, using standard oxidation procedures well known in the chemical literature.

The preparation of compounds of Formula (I) using the methods described above is demonstrated in the following examples. In these examples, temperatures are given in degrees Celsius. The compositions of solvent mixtures used as chromatographic eluents are given in percentages by volume. Abbreviations for nuclear magnetic resonance (NMR) spectra are as follows: s=singlet, d=doublet, t=triplet, q=quartet, m=multiplet; $CDCl_3$=deuterochloroform solvent, DMSO-d6=deutero-dimethylsulfoxide solvent. Peak positions for NMR spectra are reported as parts per million downfield from the internal standard tetramethylsilane. Abbreviations for mass spectra are: EI=electron impact ionization; CI=methane chemical ionization. Ether refers to diethyl ether, DMF refers to N,N-dimethylformamide, and DMSO refers to dimethylsulfoxide. Specific rotations are obtained at ambient temperature.

EXAMPLE 1a

Preparation of
1,1-bis(4-fluorophenyl)-4-(1-imidazolyl)butanol

Part A. A solution of imidazole (17.0 g, 0.25 mole) in benzene (200 mL) at room temperature was treated with sodium hydride (60% w/w oil dispersion; 8.0 g, 0.20 mole) and heated at reflux for 1 hour. After cooling to room temperature, a solution of ethyl 4-bromobutyrate (30.0 g, 0.20 mole) in benzene (50 mL) was added. The resulting mixture was again heated at reflux for 20 hours. After cooling to room temperature, the solution was washed with water, dried ($MgSO_4$) and concentrated under reduced pressure. The residual yellow oil was subjected to kugelrohr distillation at 125°–135° under rotary vacuum pump pressure to provide ethyl 4-(1-imidazolyl)butyrate as a colorless liquid (11.0 g, 30% yield). NMR($CDCl_3$) 7.44(1H,s) 7.04(1H,s) 6.90(1H,s) 4.12(2H,q,J=7 Hz) 4.02(2H,t,J=8 Hz) 2.24(2H,t,J=8 Hz) 2.08(2H,m) 1.31(3H,t,J=7 Hz).

Part B. A solution of 4-fluorobenzenemagnesium bromide was prepared in ether (60 mL) from 4-fluorobromobenzene (23.35 g, 0.133 mole) and magnesium chips (3.53 g, 0.145 mole). This mixture was cooled to 0%, and a solution of the product of Part A (10.5 g, 0.058 mole) in ether (40 mL) was added. The mixture was then heated at reflux for 20 hours, cooled to room temperature, and diluted with ethyl acetate. After adding saturated aqueous ammonium chloride, the mixture was washed sequentially with water and brine, then dried ($MgSO_4$) and concentrated under reduced pressure. The residual solid was triturated with ether, then recrystallized from 1,2-dichloroethane to provide the title compound as a white crystalline solid (6.0 g, 32%). mp 112°–114°. NMR($CDCl_3$) 7.33(4H,m) 7.10(1H,s) 6.98(4H,t,J=8 Hz) 6.76(1H,s) 4.70(1H,b) 3.88(2H,t,J=6 Hz) 2.14(2H,m) 1.77(2H,m). Mass spec (CI) m/z 329(100%).

Representative compounds of Formula (I) which can be prepared using the procedure of Example 1a are given in the following table.

TABLE 1

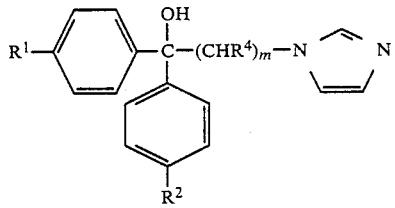

| Ex. | $R^1$ | $R^2$ | $R^4$ | m | Yield | mp (°C.) |
|---|---|---|---|---|---|---|
| 1a | F | F | H | 3 | 32% | 112–114 |
| 1b | F | F | H | 2 | 12% | 118–120 |

EXAMPLE 2a

Preparation of 1,1-bis(4-chlorophenyl)-2-(1-imidazolyl)-ethanol

Part A. A solution of 4-chlorobenzenemagnesium bromide was prepared in ether (800 mL) from 4-bromochlorobenzene (114.9 g, 0.6 mole) and magnesium chips (15.1 g, 0.62 mole). This mixture was cooled to 0°, and a solution of ethyl chloroacetate (24.5 g, 0.2 mole) was added dropwise. When addition was complete, stirring was continued at 0° for an additional hour. 1 N hydrochloric acid was then added, and the mixture extracted with dichloromethane. The organic phase was washed with water, dried (MgSO$_4$) and concentrated under reduced pressure. The residue was distilled in a kugelrohr apparatus at 0.1 torr and 180°-200° to provide 1,1-bis(4-chlorophenyl)-2-chloroethanol (43.1 g, 71%) as an oil. NMR(CDCl$_3$) 7.33(8H,m) 4.11(2H,s) 3.17(1H,s). IR (neat film) 3551 cm$^{-1}$.

Part B. A solution of imidazole (2.26 g, 33.2 mmole) in DMF (20 mL) was treated at room temperature with potassium tert-butoxide (3.72 g, 33.2 mmole) and stirred for 20 minutes. A solution of the product of Part A (5.00 g, 16.6 mmole) in DMF (20 mL) was added dropwise, and the mixture heated to 100°. After 4 hours, the solution was cooled and diluted with water. The bulk of the DMF was removed under reduced pressure, and the residual mixture was diluted with brine and extracted with ethyl acetate. The organic extracts were dried (MgSO$_4$) and concentrated under reduced pressure. The residue was stirred in ether and filtered to provide a yellow powder, which was digested in a mixture of n-butyl chloride and ethyl acetate, then recrystallized from ethyl acetate/isopropanol to provide the title compound (1.9 g, 34%) as a white crystalline solid, mp 208°-210°. NMR(DMSO-d6) 7.47(4H,d,J=10 Hz) 7.37(4H,d,J=10 Hz) 7.28(1H,s) 6.81(1H,s) 6.67(1H,s) 6.43(1H,s) 4.82(2H,s). Mass spec (CI) m/z 333(100%) 335(62%).

EXAMPLE 2b

Preparation of 1-(4-fluorophenyl)-1-(4-bromophenyl)-2-(1-imidazolyl)-ethanol Part A. A solution of 1,4-dibromobenzene (20.0 g, 0.08 mole) in tetrahydrofuran (200 mL) was cooled to −70+ and treated dropwise with n-butyllithium (1.6 M in hexane; 50 mL, 0.08 mole). The solution was stirred at this temperature for 60 minutes, then was treated dropwise with 4-fluorophenacyl chloride (13.8 g, 0.08 mole). The reaction was stirred at −70° overnight, then warmed to 0° for 3 hours. Saturated aqueous ammonium chloride was added, and the aqueous phase was separated. The aqueous phase was extracted with dichloromethane, and the combined organic phases were washed with saturated brine, then dried (Na$_2$SO$_4$) and concentrated under reduced pressure. The crude product was chromatographed on silica gel with 9:1 hexane/ethyl acetate to provide 2-(4-fluorophenyl)-2-(4-bromophenyl)-oxirane as an oil (10.5 g, 45% yield). NMR (CDCl$_3$) 7.5-6.9(8H), 3.3-3.1(2H).

Part B. A solution of the product of Part A (10.5 g, 0.035 mole) in DMF (100 mL) was treated with imidazole (6.0 g, 0.088 mole) and potassium t-butoxide (9.87 g, 0.088 mole), and the mixture was warmed to 90° and stirred overnight. The cooled mixture was poured into water and extracted with ethyl acetate. The organic phase was washed with water and saturated brine, dried (Na$_2$SO$_4$) and concentrated under reduced pressure. The resulting oil was stirred in ether for 1.5 hours, and the precipitated product was collected by filtration. After recrystallization from acetonitrile, the title compound was obtained as white crystals (8.2 g, 65% yield), m.p. 176°-178°. NMR(DMSO-d$_6$) 7.6-7.1(8H) 6.80(1H,s) 6.67(1H,s) 6.35(1H,s) 4.80(2H,s). Mass spec (CI) m/z 363(96%) 361(100%).

Representative compounds of Formula (I) which can be prepared using the procedure of Examples 2a or 2b are given in the following table.

TABLE 2

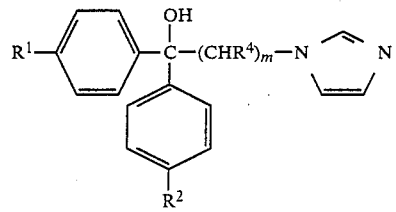

| Ex. | R$^1$ | R$^2$ | R$^4$ | m | Yield | mp (°C.) |
|---|---|---|---|---|---|---|
| 2a | Cl | Cl | H | 1 | 34% | 208-210 |
| 2b | F | Br | H | 1 | 65% | 176-178 |
| 2c | F | F | H | 1 | 11% | 202-204 |

EXAMPLE 3a

Preparation of racemic 1,1-bis(4-fluorophenyl)-2-(1-imidazolyl)butanol

Part A. A solution of n-propyltriphenylphosphonium bromide (57.8 g, 0.15 mole) in DMSO (250 mL) was treated at room temperature with potassium tertbutoxide (16.8 g, 0.15 mole). After stirring for 3 hours, the mixture was cooled to 0°, and a solution of 4,4'-difluorobenzophenone (21.8 g, 0.1 mole) in DMSO (100 mL) was added. The resulting mixture was stirred at room temperature for 18 hours, then was diluted with water and hexane. The precipitated solid was removed by filtration, and the organic phase was separated, washed with water and with brine, dried (MgSO$_4$) and concentrated under reduced pressure. The residue was distilled on a kugelrohr apparatus at 0.1 torr and 100°-110° to provide 1,1-bis(4-fluorophenyl)butene (23.9 g, 98%) as a colorless liquid. NMR(CDCl$_3$) 7.25-6.90(8H,m) 6.00(1H,t,J=6 Hz) 2.10(2H,m) 1.04(3H,t,J=6 Hz). MS (EI) m/z 244(100%).

Part B. A solution of the product from Part A (5.0 g, 20 mmole) in dichloromethane was stirred at 0°. Aqueous solutions of sodium dihydrogen phosphate (0.1 M, 25 mL) and sodium monohydrogen phosphate (0.1 M, 100 mL) were added, followed by m-chloroperoxybenzoic acid 80-85%; (4.42 g, 22 mmole). The mixture was stirred rapidly for 30 minutes, at which time additional m-chloroperoxybenzoic acid (1.62 g, 8 mmole) was added. Stirring was continued at 0% for 4 hours, then the mixture was diluted with additional dichloromethane, washed sequentially with 10% w/v aqueous sodium thiosulfate, saturated aqueous sodium becarbonate, and water, and then dried (MgSO$_4$) and concentrated under reduced pressure. The residual oil (5.4 g), consisting largely of 2,2-bis(4-fluorophenyl)-3-ethyloxirane, was used without further purification. NMR(CDCl$_3$) 7.30 (4H,m) 7.06(4H,m) 3.32(1H,t,J=5 Hz) 1.38(2H,m) 1.00(3H,t,J=6 Hz). Mass spec (CI) m/z 261(33%), 123(100%).

Part C. A solution of the product from Part B (5.0 g, 19.2 mmole) in DMF (55 mL) was stirred at room temperature. 18-Crown-6 (0.49 g, 1.9 mmole) and potassium imidazole (5.11 g, 48 mole) were added. The mixture was stirred at 90° for 20 hours, then cooled and diluted with a 1:1 mixture of ether and ethyl acetate (500 mL). The solution was washed with water, then with brine, dried (MgSO$_4$) and concentrated under reduced pressure. The residual solid was triturated with ether and collected by filtration to provide the title compound (5.15 g, 82%) as a white solid, mp 188°–190°. NMR(CDCl$_3$) 7.46(2H,m) 7.18(1H,s) 7.07(4H,m) 6.78(4H,m) 4.56(1H,dd,J=10,3 Hz) 1.88(3H,m) 0.75(3H,t,J=7 Hz). Mass spec (CI) m/z 329 (100%).

Representative compounds of Formula (I) which can be prepared using the procedure of Example 3a are given in the following table:

TABLE 3

R$^1$—⟨phenyl⟩—C(OH)(⟨phenyl⟩-R$^2$)—(CHR$^4$)$_m$—N⟨imidazole⟩N

| Ex. | R$^1$ | R$^2$ | R$^4$ | m | Yield | mp (°C.) |
|---|---|---|---|---|---|---|
| 3a | F | F | C$_2$H$_5$ | 1 | 82% | 188–190 |
| 3b | F | F | CH$_3$ | 1 | 83% | 199–201 |
| 3c | F | F | nC$_3$H$_7$ | 1 | 74% | 189–192 |
| 3d | H | H | CH$_3$ | 1 | 49% | 216–218 |
| 3e | Cl | Cl | CH$_3$ | 1 | 85% | 190–191 |

EXAMPLE 4a

Preparation of the (S)-1,1-bis(4-methylphenyl)-2-(1-imidazolyl)propanol

Part A. A solution of 4-bromotoluene (53.0 g, 0.31 mole) in tetrahydrofuran (400 mL) was stirred at −75° and treated dropwise with n-butyllithium (1.6 M in hexane; 194 mL, 0.31 mole). After stirring for an additional 20 minutes, (S)-ethyl lactate (11.8 g, 0.1 mole) was added dropwise as a solution in tetrahydrofuran (20 mL). The reaction was stirred for three hours, during which time the temperature was allowed to rise to room temperature. Saturated aqueous ammonium acetate was added, after which the reaction mixture was diluted with ether, washed with water and brine, dried (MgSO$_4$) and concentrated under reduced pressure. (S)-1,1-bis(4-methyl-phenyl)-1,2-propanediol (27 g) was isolated as a pale yellow solid, and was used without further purification. NMR(CDCl$_3$) 7.44(2H,d,J=8 Hz) 7.28(2H,d,J=8 Hz) 7.13(2H,d,J=8 Hz) 7.06(2H,d,J=8 Hz) 4.74(1H,q,J=6 Hz) 2.97(1H,broad) 2.29(6H,2s) 1.90(1H,braod s) 1.10(3H,d,J=6 Hz).

Part B. A solution of the product of Part A (5.0 g, 20.5 mmole) in ether (100 mL) was stirred at 0°, and treated with triethylamine (2.5 g, 24.6 mmole) and methanesulfonyl chloride (2.9 g, 25.6 mmole). The mixture was stirred for 2 hours at room temperature, then treated with saturated aqueous ammonium chloride and extracted with ethyl acetate. The organic phase was washed with water and brine, dried (MgSO$_4$) and concentrated under reduced pressure to provide (S)-1,1-bis(4-methylphenyl)-2-methanesulfonyloxy-1-propanol (6.8 g, 99%) as an off-white solid, mp 83°–85°. NMR(CDCl$_3$) 7.46(2H,d,J=7 Hz) 7.33(2H,d,J=7 Hz) 7.15(4H,t,J=7 Hz) 5.69(1H,q,J=6 Hz) 2.58(3H,s) 2.30(6H,broad s) 1.43(3H,d,J=6 Hz). This material was used without further purification.

Part C. A solution of the product of Part B (6.7 g, 20 mmole) in DMF (75 mL) was treated with 18-crown-6 (0.4 g, 1.5 mmole) and potassium imidazole (6.4 g, 60 mmole) and stirred at 90° for 20 hours. The mixture was cooled, diluted with 1:1 ether/ethyl acetate, and washed with water and brine. The organic phase was dried (MgSO$_4$) and concentrated under reduced pressure. The residue was recrystallized from n-butyl chloride to provide the title compound (2.0 g, 33%) as white needles, mp 194°–196°. NMR(CDCl$_3$) 7.40(2H,d,J=7 Hz) 7.17(3H,d,J=7Hz) 7.07(2H,d,J=7 Hz) 6.94(2H,d,J=7 Hz) 6.82(1H,s) 6.70(1H,s) 5.04(1H,q,J=6 Hz) 3.70(1H,broad) 2.33(3H,s) 2.20(3H,s) 1.48(3H,d,J=6 Hz). Mass spec (CI) m/z 307(100%). [α]$_D$ +209° (c 0.4, EtOH).

Representative compounds of Formula (I) which can be prepared using the procedure of Example 4a are given in the following table.

TABLE 4

R$^1$—⟨phenyl⟩—C(OH)(⟨phenyl⟩-R$^2$)—(CHR$^4$)$_m$—N⟨imidazole⟩N

| Ex. | R$^1$ | R$^2$ | R$^4$ | m | Yield | mp (°C.) |
|---|---|---|---|---|---|---|
| 4a | CH$_3$ | CH$_3$ | CH$_3$ | 1 | 33% | 194–196 |
| 4b | F | F | CH$_3$ | 1 | — | 180–182 |
| 4c | Cl | Cl | CH$_3$ | 1 | — | 164–166 |

EXAMPLE 5a

Preparation of the (R)-1,1-bis(4-chlorophenyl)-2-(1-imidazolyl)propanol

Part A. A solution of 4-bromochlorobenzene (63.2 g, 0.33 mole (in tetrahydrofuran (600 mL) was stirred at −75° and treated dropwise with n-butyllithium (1.55 M in hexane; 213 mL, 0.33 mole). After stirring the mixture for an additional 30 minutes, a solution of (R)-ethyl 2-chloropropionate (22.3 g, 0.15 mole) in tetrahydrofuran (50 mL) was added dropwise. The reaction was then allowed to warm to room temperature, stirred for 18 hours, and treated with saturated aqueous ammonium chloride. The mixture was then extracted with ether, and the organic phase was washed with water and brine. Drying (MgSO$_4$) and concentration under reduced pressure provided (S)-1,1-bis(4-chlorophenyl)-2-methyloxirane (46.5 g) as a red liquid which was used without further purification. Part B. A solution of the product from Part A (44.1 g, 0.16 mole) in DMF (400 mL) was treated with imidazole (26.9 g, 0.40) and potassium tertbutoxide (44.3 g, 0.40 mole) and stirred at 90° for 20 hours. The mixture was cooled to room temperature and diluted with 1:1 ether/ethyl acetate, then washed with water and brine. Drying (MgSO$_4$) and concentration provided a tan glass which was stirred overnight in ether. The resulting white powder was collected by filtration to provide the title compound (34.9 g, 64%), mp 159°–161°. NMR(CDCl$_3$) 7.43(2H,d,J=7 Hz) 7.30(2H,d,J=7 Hz) 7.10(1H,s)

7.03(4H,s)  6.72(1H,s)  6.47(1H,s)  5.6(1H,broad) 4.94(1H,q,J=6 Hz) 1.44(3H,d,J=6 Hz). Mass spec (CI) m/z 347(100) 349(66). $[\alpha]_D$ -185° (c 2, EtOH).

Representative compounds of Formula (I) which can be prepared using the procedure of Example 5a are given in the following table.

TABLE 5

$$R^1 \diagdown \diagup \diagdown C(OH)(-CH-N\diagdown N)(CH_3)-C_6H_4-R^2$$

| Ex. | $R^1$ | $R^2$ | Yield | mp (°C.) |
|---|---|---|---|---|
| 5a | 4-Cl | 4-Cl | 64% | 159–161 |
| 5b | 4-F | 4-F | 59% | 181–183 |
| 5c | 4-CH$_3$ | 4-CH$_3$ | 48% | 197–198 |
| 5d | 3-Cl | 3-Cl | 36% | 198–199 |
| 5e | 4-CF$_3$ | 4-CF$_3$ | 61% | 166–168 |
| 5f | 4-CH$_3$S | 4-CH$_3$S | 50% | 206–208 |

Utility

Various observations have established a possible role for arachidonic acid metabolites, such as leukotrienes and prostaglandins, in the pathogenesis of skin inflammatory diseases such as psoriasis and contact dermatitis. Reduction in the levels of these metabolites is associated with improvement in the lesions. The arachidonic acid is released by the action of a phospholipase on cell membrane (for a review, see Voorhees, Arch. Dermatol. 119, p. 541, 1983). Antiinflammatory steroids are effective in treating skin inflammatory diseases. However, these steroids have significant side effects which include skin atrophy and rebound of symptoms upon cessation of therapy. The mode of action of antiinflammatory steroids is not completely understood, but it has been related to the induction of an antiinflammatory protein which inhibits the release of arachidonic acid. The classic non-steroidal antiinflammatory drugs, which inhibit prostaglandin biosynthesis only, are not effective in the treatment of skin inflammatory diseases in general. The above observations have led to a search for inhibitors of either the phospholipase step or dual inhibitors of both the leukotriene and cyclooxygenase pathway.

The compounds of this inention have been shown to be efficacious in murine models of skin inflammatory diseases in which inflammatory metabolites of arachidonic acid are produced. One such model is the inflammation induced by tetradecanoyl phorbol acetate (TPA). The test methods are modified from those of Marks et al. (Cancer Res, 36, p. 2636, 1976). The TPA model is a murine model which mimics many of the inflammatory changes which occur in human disease such as psoriasis. In this model, elevated levels of inflammatory arachidonic acid metabolites are found, and an influx or polymorphonuclear leukocytes (PMN) is observed. The procedure used to evaluate the compounds of this invention is as follows: the test compound (100 μg/ear) is applied to the ears of mice in an appropriate vehicle, such as acetone, and then the inflammatory stimulus is applied to the right ear. Four hours later, the edema is measured by removing standard sized discs from the mouse ears using a biopsy punch. The masses of the discs are then determined.

Results obtained in the model for selected compounds of Formula (I) are shown in Table 6. Some of the compounds useful in this invention have also been shown to reduce the levels of both the arachidonic acid metabolites and the numbers of PMN in murine skin inflamed with TPA.

TABLE 6

| Example | % Inhibition of Control Inflammation |
|---|---|
| 1a | 31% |
| 2b | 41% |
| 3a | 40% |
| 3b | 40% |
| 3c | 30% |
| 3e | 55% |
| 4a | 33% |
| 4b | 50% |
| 4c | 61% |
| 5a | 61% |
| 5b | 48% |
| 5d | 39% |
| 5e | 49% |
| 5f | 31% |

Topical Formulations

The topical pharmaceutical compositions according to the invention may, for example, take the form of ointments, gels, pastes, creams, sprays (including aerosols), lotions, suspensions, solutions, emulsions, liposomes and patches of the active ingredient in aqueous or non-aqueous diluents, syrups, granulates or powders.

The diluents to be used in pharmaceutical compositions which are ointments, pastes, creams, and gels can, for example, contain the usual diluents, e.g., waxes, paraffins, starch, polyethylene glycol, silicones, bentonites, silicic acid, animal and vegetable fats, talc and zinc oxide or mixtures of these diluents.

The pharmaceutical compositions which are solutions and emulsions can, for example, contain the customary diluents (with the exclusion of solvents having a molecular weight below 200 except in the presence of a surface-active agent), such as solvents, dissolving agents and emulsifiers; specific examples are water, ethanol, isopropanol, ethyl carbonate, benzyl alcohol, propylene glycol, oils (for example, ground nut oil), glycerol, and fatty acid esters of sorbitol or mixtures thereof.

The pharmaceutical compositions which are powders and sprays can, for example, contain the usual diluents, e.g., lactose, talc, silicic acid, aluminum hydroxide, calcium silicate, and polyamide powder or mixtures of these materials. Aerosol sprays can, for example, contain the usual propellents. Liposomes can be made from such materials as animal or vegetable fats which will form lipid bilayers in which the compounds of this invention can be incorporated.

The pharmaceutical compositions which are patches can be made of a matrix such as polyacrylamide, and a semipermeable membrane made from a suitable polymer to control the rate at which the material is deliverd to the skin.

For example, an ointment for topical administration may be prepared by adding the active ingredient to a mixture of 48% by weight white petrolatum, 10% liquid petrolatum, 8% glycerol monostearate, 3% isopropyl myristate and 20% lanolin at 70%. After through mixing, a warm solution of methyl and propyl parabens in water containing sodium acetone bisulfite is added such that the final concentrations of each paraben is 0.15%, of water is 8% and of sodium acetone bisulfite is 0.5%.

The mixture is stirred until it has reached room temperature. The final concentration of the active ingredient in between about 0.5% and 10% by weight.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A topical pharmaceutical composition consisting essentially of a suitable pharmaceutical carrier and an antiinflammatory amount of a compound of the formula:

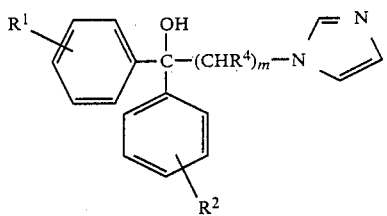

or a pharmaceutically accetable salt thereof,
wherein $R^1$ and $R^2$ independently are H, F, Cl, Br, $CH_3$, $CF_3$ or $S(O)_nR^3$ where n is 0, 1 and 2 and $R^3$ is alkyl of 1-4 carbon atoms;

$R^4$ is H or alkyl or 1-4 carbon atoms with the proviso that $R^4$ is H when m is 2 or 3; and m is 1 to 3.

2. A composition of claim 1 wherein m is 1 and $R^4$ is $CH_3$.

3. A composition of claim 1 wherein $R^1$ and $R^2$ are both 4-Cl or 4-F.

4. A composition of claim 1 wherein the compound is 1,1-bis(4-chlorophenyl)-2-(1-imidazolyl)propanol.

5. A composition of claim 1 wherein the compound is 1,1-bis(4-fluorophenyl)-2-(1-imidazolyl)propanol.

6. A method of treating inflammation in a mammal, comprising administering topically to the mammal an antiinflammatory amount of a compound of the formula

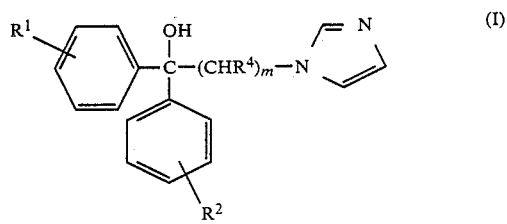

or a pharmaceutically acceptable salt thereof,
wherein $R^1$ and $R^2$ independently are H, F, Br, Cl, $CH_3$, $CF_3$ or $S(O)_nR^3$ where n is 0, 1 or 2 and $R^3$ is alkyl of 1-4 carbon atoms;

$R^4$ is H or alkyl of 1-4 carbon atoms with the proviso that $R^4$ is H when m is 2 or 3; and m is 1 to 3.

7. A method of claim 6 wherein m is 1 and $R^4$ is $CH_3$.

8. A method of claim 6 wherein $R^1$ and $R^2$ are both 4-Cl or 4-F.

9. A method of claim 6 wherein the compound is wherein the compound is 1,1-bis(4-chlorophenyl)-2-(1-imidazolyl)propanol.

10. A method of claim 6 wherein the compound is 1,1-bis(4-chlorophenyl)-2-(1-imidazolyl)propanol.

* * * * *